US009048074B2

(12) United States Patent
Senko (10) Patent No.: US 9,048,074 B2
(45) Date of Patent: Jun. 2, 2015

(54) MULTINOTCH ISOLATION FOR MS³ MASS ANALYSIS

(71) Applicant: Thermo Finnigan LLC, San Jose, CA (US)

(72) Inventor: Michael W. Senko, Sunnyvale, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

(21) Appl. No.: 14/374,035

(22) PCT Filed: Jan. 24, 2013

(86) PCT No.: PCT/US2013/022879
§ 371 (c)(1),
(2) Date: Jul. 23, 2014

(87) PCT Pub. No.: WO2013/112677
PCT Pub. Date: Aug. 1, 2013

(65) Prior Publication Data
US 2014/0339421 A1     Nov. 20, 2014

Related U.S. Application Data

(60) Provisional application No. 61/590,280, filed on Jan. 24, 2012.

(51) Int. Cl.
    *H01J 49/00*     (2006.01)
    *H01J 49/42*     (2006.01)
    *G01N 33/68*     (2006.01)

(52) U.S. Cl.
    CPC ......... *H01J 49/0045* (2013.01); *H01J 49/0081* (2013.01); *H01J 49/428* (2013.01); *G01N 33/6848* (2013.01); *H01J 49/0031* (2013.01)

(58) Field of Classification Search
USPC .................................................. 250/281, 282
See application file for complete search history.

(56) References Cited

U.S. PATENT DOCUMENTS

| 5,179,278 A | 1/1993 | Douglas |
|---|---|---|
| 2003/0213908 A1 | 11/2003 | Umemura |
| 2005/0067565 A1 | 3/2005 | Takada et al. |
| 2009/0194688 A1 | 8/2009 | Bateman et al. |
| 2011/0111513 A1 | 5/2011 | Baumann et al. |
| 2013/0084645 A1* | 4/2013 | Coon et al. ..................... 436/173 |

OTHER PUBLICATIONS

Ting et al., "MS3 eliminates ratio distortion in isobaric multiplexed quantitative proteomics," Nature Methods, vol. 8, No. 11 (2011), pp. 937-942.

(Continued)

*Primary Examiner* — Kiet T Nguyen
(74) *Attorney, Agent, or Firm* — Thomas F. Cooney (57) ABSTRACT

A mass spectrometry method for analyzing isobarically-labeled analyte compounds comprising (a) ionizing compounds including the isobarically-labeled analyte compounds to generate a plurality of precursor ion species comprising different respective m/z ratios, (b) isolating a precursor ion species, (c) fragmenting the precursor ion species to generate a plurality of first-generation fragment ion species comprising different respective m/z ratios, and (d) selecting and co-isolating two or more of the first-generation product-ion species, the method characterized by: (e) fragmenting all of the selected and isolated first-generation product ion species so as to generate a plurality of second-generation fragment ion species including released label ions; (f) generating a mass spectrum of the second-generation fragment ion species; and (g) generating quantitative information relating to at least one analyte compound based on peaks of the mass spectrum attributable to the released label ions.

10 Claims, 6 Drawing Sheets

(56) References Cited

OTHER PUBLICATIONS

McAlister et al., "Increasing the Multiplexing Capacity of TMTs Using Reporter Ion Isotopologues with Isobaric Masses," Anal. Chem., 2012, 84, pp. 7469-7478.

Chang, et al., "iTRAQ-IT: Implementation of iTRAQ™ Quantitation Tags on Ion Trap Instruments via MS3," Poster, 53rd Annual American Society for Mass Spectrometry Meeting, San Antonio (2005).

Kiyonami, et al., "Identification and Quantification of iTRAQ Labeled Peptides on the Finnigan LTQ using MS/MS and MS3," Thermo Electron Corporation, Application Note: 353 (2005), pp. 1-4.

* cited by examiner

MULTINOTCH ISOLATION FOR MS³ MASS ANALYSIS

TECHNICAL FIELD

The present invention relates to proteomics and the identification and quantification of polypeptides using mass spectrometry.

BACKGROUND ART

Mass spectrometry has become the method of choice for fast and efficient identification of proteins in biological samples. In general, a mass spectrometer comprises an ion source for generating ions from molecules to be analyzed, and ion optics for guiding the ions to a mass analyzer. A tandem mass spectrometer further comprises the ability to perform a second stage of mass analysis. As is well known, the second stage of mass analysis may be performed using a tandem-in-space configuration employing more than one analyzer or in a tandem-in-time configuration, using only a single analyzer. In tandem mass spectrometry, structural elucidation of ionized molecules is performed by collecting a mass spectrum, then using a first mass analyzer to select a desired precursor ion or ions from the mass spectrum, causing fragmentation of the selected precursor ions, and then performing mass analysis of the fragment ions using a second stage of mass analysis.

Tandem mass spectrometry of peptides in a complex protein mixture can be used to identify and quantify the proteins present in the original mixture. Tandem mass spectrometers achieve this by selecting single m/z values and subjecting the precursor ions to fragmentation, providing product ions that can be used to sequence and identify peptides. This method can be extended to provide one or more further stages of fragmentation (i.e. fragmentation of fragment ions and so on). This is typically referred to as MS$^n$, with the superscript "n" denoting the number of generations of ions. Thus MS$^2$ corresponds to tandem mass spectrometry.

In many research and clinical applications, it is desirable to not only to identify peptides or proteins according to their amino acid composition, but also to quantify these analytes according to their respective sources. Isotopic labels have been extensively employed for the latter purpose. Recently, labels which are categorized as so-called "isobaric tags" have been developed in order to overcome the problems that: (a) native peptides and deuterium-labeled peptides frequently do not precisely co-elute (b) the isotopically-labeled peptides often give rise to charge states, upon electrospray ionization, that are different from those of the non-labeled peptides (A. Thompson et al., "Tandem Mass Tags: A Novel Quantification Strategy for Comparative Analysis of Complex Protein Mixtures by MS/MS", *Anal. Chem.* 2003, 75, 1895-1904).

A first isobaric labeling technique employs sets of reagents known as tandem mass tags (ibid.) which provide labels comprising a mass reporter region, a cleavable linker region, a mass-normalization region and a reactive group. Different samples of a single peptide, when labeled with different respective tandem mass tag (TMT) reagents, will all comprise the same chemical structure and mass and will therefore co-elute. However, upon mass spectrometric analysis by collision-induced dissociation, an ion is released that has a specific mass-to-charge ratio that is diagnostic of a specific tag, thereby enabling identification of the source of the peptide or protein. A second isobaric labeling technique, known as "isobaric tags for relative and absolute quantitation" or (iTRAQ) employs isobaric mass labels attached to the N termini and lysine side chains of peptides in a digest mixture. As in the TMT technique, all differentially-labeled samples of a single analyte will comprise the same chemical structure and mass. Upon undergoing collision induced dissociation, however, signature or reporter ions are released that can be used to identify and quantify individual proteins according to their respective sources or treatments. The iTRAQ technique is described in P. L. Ross et al., "Multiplexed Protein Quantitation in *Saccharomyces cerevisiae* Using Amine-reactive Isobaric Tagging Reagents", *Molecular and Cellular Proteomics* 2004, 3, 1154-1169.

In either the TMT or iTRAQ technique, precursor ions comprising particular mass-to-charge (m/z) ratios corresponding to expected or known peptides are isolated. These precursor ions are then fragmented by collision-induced dissociation so as to both cleave the peptide backbone as well to fragment the tags. Sequence information may then be obtained from analysis of the fragments produced by the backbone cleavage and source identification may be revealed by analysis of reporter ions produced by fragmentation of the tags.

Recently, it has been realized that the use of isobaric tags for quantitation of peptides and proteins is affected by inherent interferences that fall within the initial m/z isolation window. These interferences are due to unrelated co-eluting peptides that fall within the isolation window for the precursor of interest. Since the vast majority of peptides have unchanged ratios between control and experiment, the interferences tend to drag all ratios towards unity, and thus its difficult to obtain accurate quantitative values.

Several approaches have been proposed to minimize the impact of the interference. A first approach (G. M. Sweetman, "Synchronising MS/MS Analysis with The Chromatographic Peak Apex Enables More Precise and Accurate Isobaric Tag Quantification", Proc. 58th ASMS, Salt Lake City, 2010) employs triggering mass analysis at the apex of targeted chromatographic peaks (LC apex triggering), which in theory enhances the purity of the precursor, since it is examined when it is most concentrated. A second proposed approach includes the use of proton transfer reagents to reduce ion charge state and shift t precursor m/z, followed by an additional step of isolation before fragmentation (D. Bailey et al., "How High Mass Accuracy Measurements Will Transform Targeted Proteomics", 8$^{th}$ North American FT MS Conference, Key West, Fla., 2011), In another approach, termed "Quantmode", isolation purity filters are employed (C. D. Wenger et al., "A real-time data acquisition method for improved protein quantitation on hybrid mass spectrometers", Proc. 58th ASMS, Salt Lake City, 2010). The Quantmode technique involves triggering MS/MS analysis only for precursors that meet a defined purity within the intended isolation window. All the above methods provide some level of reduced interference, but still show systematic deviation of ratios towards unity.

In yet another approach (L. Ting et al., "MS 3 Eliminates Ratio Distortion in Isobaric Multiplexed Quantitative Proteomics", *Nature Methods* 2011, 8, 937-940) the use of MS$^3$ is reported. In this technique, a peptide ion is first isolated and fragmented. A selected fragment of the precursor is then itself isolated, and higher-energy dissociation (HCD) of the isolated fragment is performed to release the tag. This method is only successful because most fragments formed by ion trap CID maintain the tag. Although this method provides the most accurate tag ratios to date, it suffers from poor sensitivity, since any particular fragment is rarely more than 5% of the abundance of the initial precursor. Accordingly, there remains a need in the art for a method of analyzing isobarically tagged proteins and peptides that both minimizes interference and provides high sensitivity.

DISCLOSURE OF INVENTION

In order to address the above noted need in the art, this document discloses a new approach to the acquisition and deductive analysis of mixed-fragment peptide mass spectra. To enhance the sensitivity of the $MS^3$ technique described above, it is here noted that it is possible to co-isolate multiple fragments prior to the HCD step. This multiple-fragment isolation is fairly easy to achieve when isolating in a linear ion trap, because resonance-excitation waveforms, which are used to eject unwanted ions, may be constructed with multiple notches. Each such notch corresponds to a different respective m/z window within which ions will not be ejected (and thus isolated). This novel technique adds no time to the experiment execution, since the $MS^2$ ions are all isolated simultaneously, unlike mass filter isolation, where ions need to be passed sequentially. The use of multi-notch isolation can increase the sensitivity of the $MS^3$ experiment up to N-fold, where N is the number of $MS^2$ fragments selected and simultaneously isolated.

According to a first aspect of the invention, there is provided a method for analyzing isobarically-labeled analyte compounds using a mass spectrometer, the method comprising the steps of (a) ionizing a set of compounds including the isobarically-labeled analyte compounds provided from a sample so as to generate a plurality of precursor ion species comprising different respective mass-to-charge (m/z) ratios, (b) isolating a selected precursor ion species, (c) fragmenting the selected precursor ion species so as to generate a plurality of first-generation fragment ion species comprising different respective m/z ratios, and (d) selecting and co-isolating a subset of the plurality of first-generation product ion species comprising two or more of the first-generation product ion species, wherein the method is characterized by the steps of:

(e) fragmenting the selected and isolated first-generation product ion species so as to generate a plurality of second-generation fragment ion species including released label ions;

(f) generating a mass spectrum of the second-generation fragment ion species; and (g) generating quantitative information relating to at least one analyte compound based on peaks of the mass spectrum attributable to the released label ions.

According to another aspect of the invention, there is provided an apparatus comprising: (a) an ion source configured to so as to, generate a plurality of precursor-ion species having respective mass-to-charge (m/z) ratios from a plurality of isobarically-labeled analyte compounds comprising respective chemical labels; (b) at least one ion trap configured to receive the plurality of precursor ion species, to isolate a selected precursor ion species and to co-isolate a selected two or more of a plurality of first-generation product-ion species generated by fragmentation of the selected precursor ion species; (c) at least one fragmentation cell configured to fragment the isolated precursor ion species so as to generate the plurality of first-generation product-ion species and to fragment the selected two or more of the first-generation product-ion species so as to generate a plurality of second-generation product-ion species; and (d) a mass analyzer configured so as to separate and detect ion species of the precursor-ion species, of the plurality of first-generation product-ion species and of the plurality of second-generation product-ion species; wherein the apparatus is characterized in that:

the at least one fragmentation cell is configured so as to fragment the isolated selected precursor ion species using a fragmentation energy or mechanism that does not cause fragmentation or release of the labels of the isolated selected precursor ion species and using a fragmentation energy or mechanism that fragments the selected two or more of the first-generation product-ion species such that label ions are released.

The co-isolating a subset of the plurality of first-generation product ion species may be performed, in some embodiments, by simultaneously isolating all of the plurality of first-generation product ion species. One way of doing this is by applying a broadband resonance ejection frequency waveform to an ion trap, wherein the waveform comprises multiple summed sinusoidal frequency components, wherein included frequency components corresponding to the m/z ranges of ions that one desires to eject from the trap and excluded frequency components correspond to the m/z range of ions that one desires to retain within the trap. In this procedure, the omitted frequencies define one or more frequency notches in the ejection frequency waveform. The frequency components may be calculated by first choosing a desired multi-notch waveform and then calculating an inverse Fourier Transform of the desired waveform. Alternatively, the co-isolating of the subset of the plurality of first-generation product ion species may be performed by isolating individual precursor ion species in a conventional sense, one ion species at a time using a respective single-notch waveform, and transferring each individually isolated ion species to a fragmentation cell or to an ion storage component in which the various selected and isolated ion species are accumulated over time.

The fragmenting of the isolated precursor ion species and of the selected two or more of the first-generation product-ion species may be performed by any suitable available means, such as, for example, by collision-induced dissociation (CID), electron capture dissociation (ECD), electron transfer dissociation (ETD) or infrared multiphoton dissociation (IRMPD). In various embodiments, the two stages of fragmentation (the first stage comprising the fragmenting of the isolated precursor ion species and the second stage comprising the fragmenting of the selected two or more of the first-generation product-ion species) may be performed using different fragmentation mechanisms or different values of an applied fragmentation energy. For example, CID could be employed in the first stage using an applied collision energy that is insufficient to cause substantial fragmentation of or release of the labels, whereas higher-energy dissociation (HCD) could be employed in the second stage such that the mass tags are fragmented so as to release label ions. As another example, ETD or ECD could be employed to as to fragment proteins or peptides along the molecular structural backbone whereas a different fragmentation technique could be employed so as to release the label ions.

In some embodiments, such as when different applied fragmentation energy values are employed for the two stages of fragmentation, a single fragmentation cell may be employed. One such example is a single collision cell that may be operated using different values of applied collision energy. In other embodiments, such as when different fragmentation mechanisms are employed, then multiple fragmentation cells may be required.

In some embodiments, the isobarically-labeled analyte compounds may comprise isobarically-labeled proteins or peptides. In such cases, the fragmenting of the selected precursor ion species may be performed using a collision energy that is sufficient to cleave protein or peptide backbone bonds within the selected precursor ion species but that is insufficient to cause substantial fragmentation or release of the labels of the selected precursor ion species. In some embodiments, a material submitted for analysis may include a labeled standard compound, wherein a precursor ion species from the standard compound comprises a similar m/z ratio as a precursor ion species from an analyte compound and wherein a first-generation fragment ion species generated from the labeled standard compound comprises a similar m/z ratio as a first-generation fragment ion species generated from an analyte compound. In such cases, a concentration of the labeled analyte compound may be determined, in step (e), by comparing a detected quantity of a label ion released from the standard compound with a detected intensity of a label ion released from said the labeled analyte compound.

In various embodiments, the fragmentation of the selected two or more of the first-generation product-ion species may be performed simultaneously, such as subsequent to when the two or more of the first-generation product ion species are simultaneously isolated using multi-notch isolation as described herein. These simultaneously isolated species could be transferred as a group to a fragmentation cell for simultaneous fragmentation in the fragmentation cell so as to produce the second-generation product ion species. In other embodiments, the individual ion species comprising the selected two or more of the first-generation product-ion species could be fragmented individually, one ion species at a time. Such a technique might be employed, for instance, if the selected first-generation product-ion species are individually isolated, one species at a time. Each such isolated species might be respectively transferred to a fragmentation cell so as to be fragmented during an individual respective second stage of fragmentation.

In various embodiments, multiple isobarically-labeled analyte compounds might be analyzed simultaneously using the techniques described above. Such simultaneous analyses might be employed, for instance, if the analytes co-elute from a chromatographic system or if a mixture of analytes is infused into a mass spectrometer system. As but one example, labeled co-eluting analyte compounds "A", "B" and "C" might simultaneously give rise to distinctive precursor ion species "a", "b" and "c", respectively, when ionized in an ion source. Each of the three precursor ion species might comprise one or more subsets, each subset comprising a respective distinctive label, wherein the labeling is isobaric labeling. In other words, all ions comprising species a comprise the same mass-to-charge ratio, within the separation resolution of the mass spectrometer instrument, regardless of which label they carry. Similar statements would hold for the species b and the species c. The different labels could correspond, for example, to different samples from which the set of analyte compounds are extracted. The labels applied to the various analyte compounds need not be the same labels.

The situation of simultaneous analyses of analyte compounds A, B and C is a straightforward extension of the single-analyte analysis techniques described above. In the case of multiple simultaneous analyses, the precursor ion species a, b and c might themselves be co-isolated, prior to the first fragmentation stage. The co-isolation of the precursor ion species might be performed according to any of the techniques described herein, for instance, by using multi-notch simultaneous co-isolation. The first stage of fragmentation (so as to generate the first-generation fragment ion species) may be performed by simultaneous fragmentation of the co-isolated precursor ion species. Subsequent steps would then proceed in a fashion as already described.

BRIEF DESCRIPTION OF DRAWINGS

The above noted and various other aspects of the present invention will become apparent from the following description which is given by way of example only and with reference to the accompanying drawings, not necessarily drawn to scale, in which.

MODES FOR CARRYING OUT THE INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein. It will be understood that certain features and configurations of apparatuses are presented by way of illustrative examples, and should not be construed as limiting the invention to implementation in a specific configuration or environment. To fully appreciate the particular features and advantages of the present invention, the reader is advised to consult FIGS. 1-6 of the attached drawings in conjunction with the following discussion.

Figure 1:
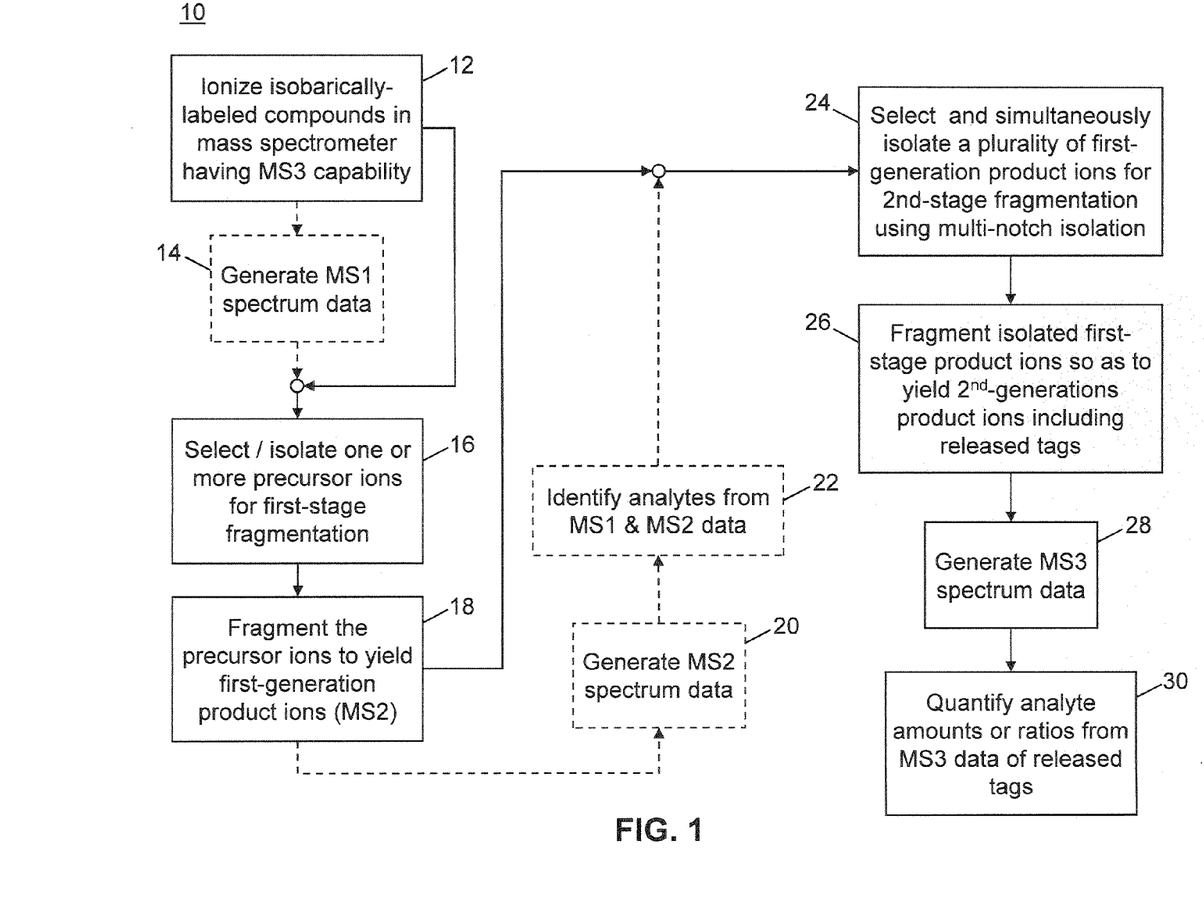
FIG. 1 is a flowchart of a method for mass spectrometric identification of peptides in accordance with the present teachings.

FIG. 1 is a flowchart of a method for mass spectrometric identification of peptides in accordance with the present teachings. Optional steps of the method 10 shown in FIG. 1 are outlined in dashed lines. In the first step, Step 12 of the method 10, isobarically-labeled compounds (analytes or standards or both) are ionized in a mass spectrometer system having $MS^3$ capability. The isobarically labeled analytes or standards may be provided to the mass spectrometer system from the eluting end of a chromatographic column. The tem "having $MS^3$ capability" means that the mass spectrometer system is capable of producing a first generation of fragment ions from precursor ions and subsequently isolating and further fragmenting the first-generation fragment ions so as to produce a second generation of fragment ions.

In the optional Step 14, of the method 10 (FIG. 1), $MS^1$ spectrum data may be generated. The $MS^1$ spectrum data, if produced, is mass spectrum data of the ions—including precursor ions—prior to fragmentation in a fragmentation or collision cell of the mass spectrometer. Although the Step 14 will generally be performed, it may be eliminated if there is a high confidence that the spectrum data will adopt a certain known form, as in the case where known materials are being introduced into the mass spectrometer.

In Step 16 of the method 10 (FIG. 1), a precursor ion provided from the ionization step (Step 12) is selected or isolated for first-stage fragmentation. This step may be accomplished in a number of ways. For example, if a single ion precursor ion is to be isolated, this single ion could be isolated using a mass filter component of the mass spectrometer, as is discussed with reference to FIG. 3.

Figure 2:
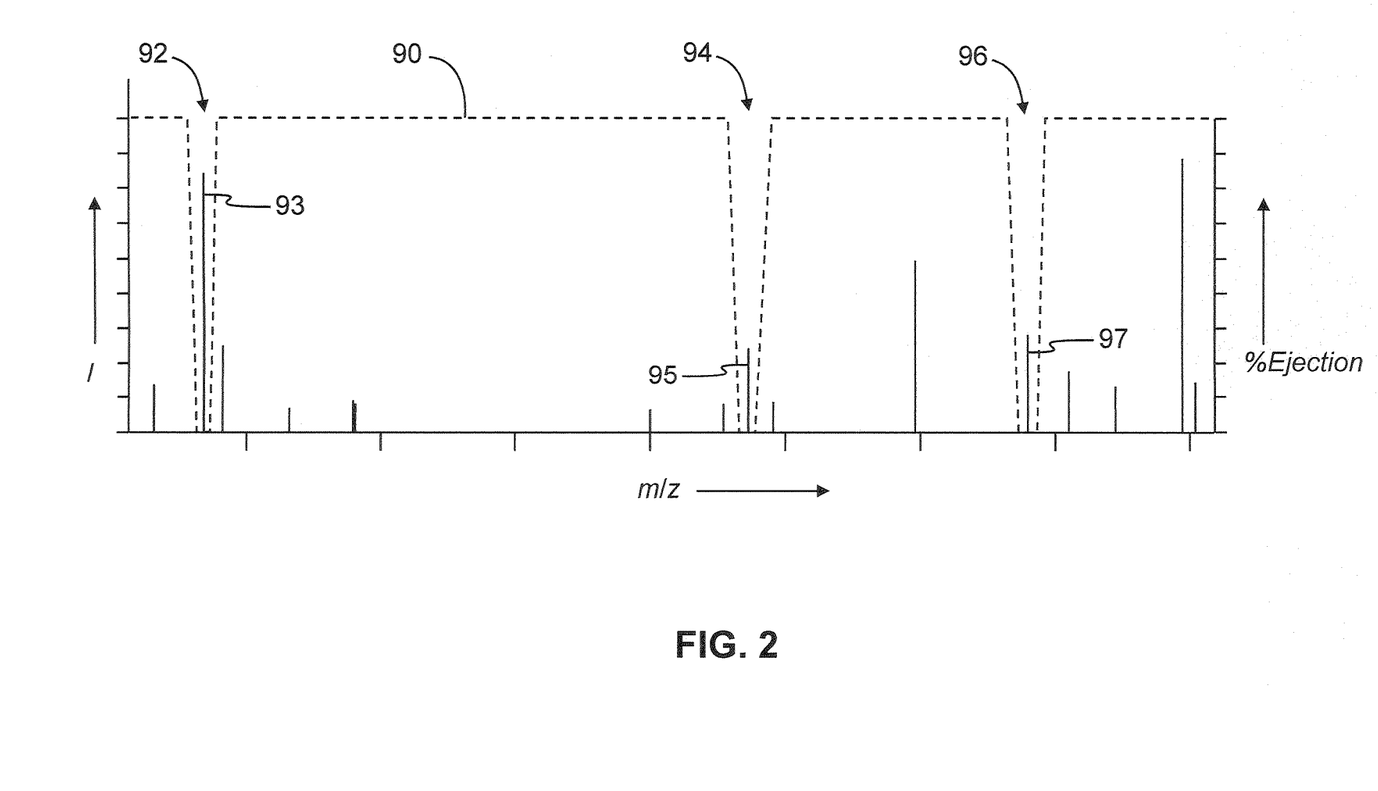
FIG. 2 is a schematic diagram of a hypothetical mass spectrum plotted together with an overlaid plot of percentage of ions ejected as a function of mass-to-charge ratio when multi-notch ion isolation is applied.
Figure 3:
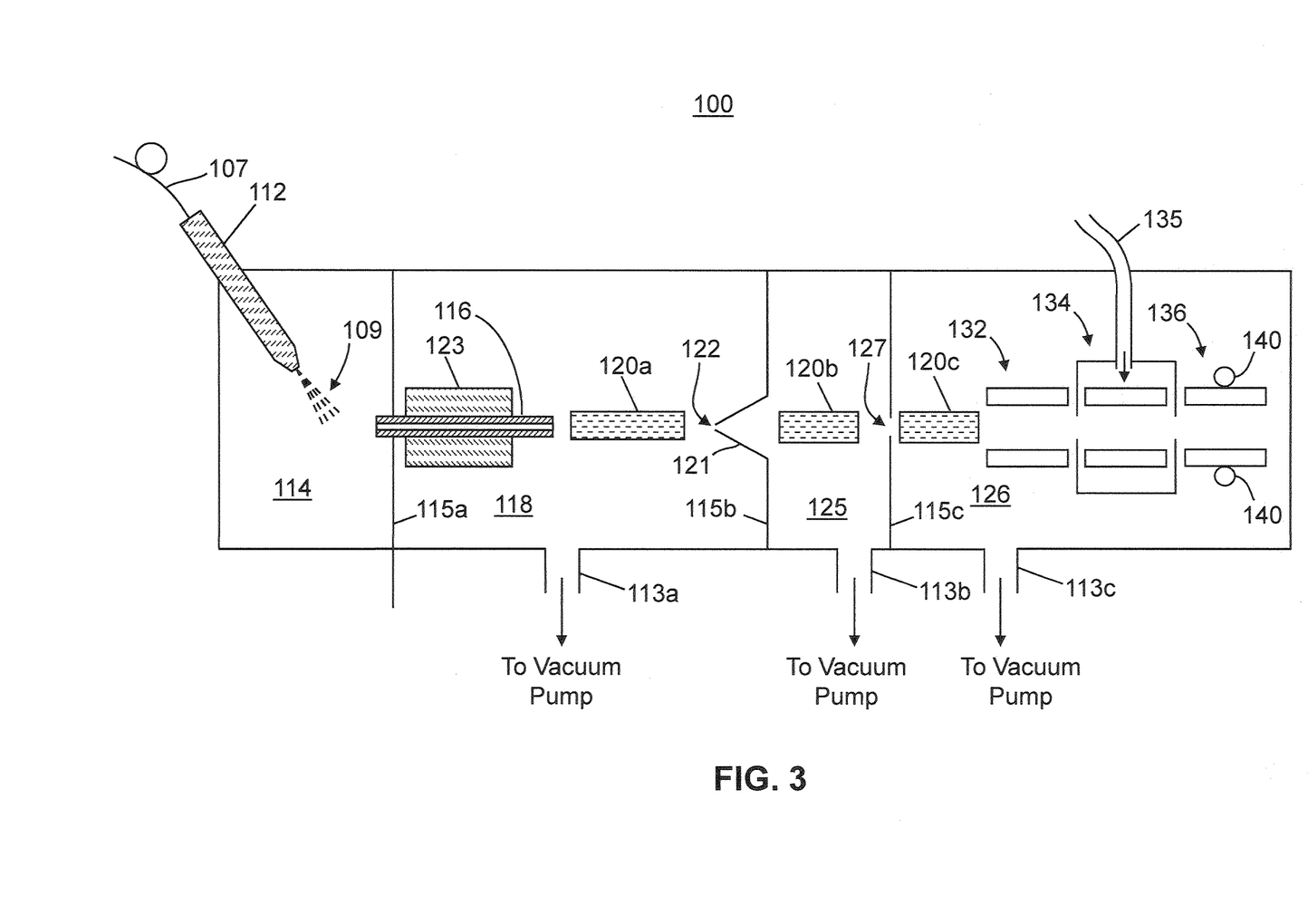
FIG. 3 is a schematic illustration of an example of a conventional ion trap mass spectrometer in which collisional ion dissociation may be performed.
Figure 4:
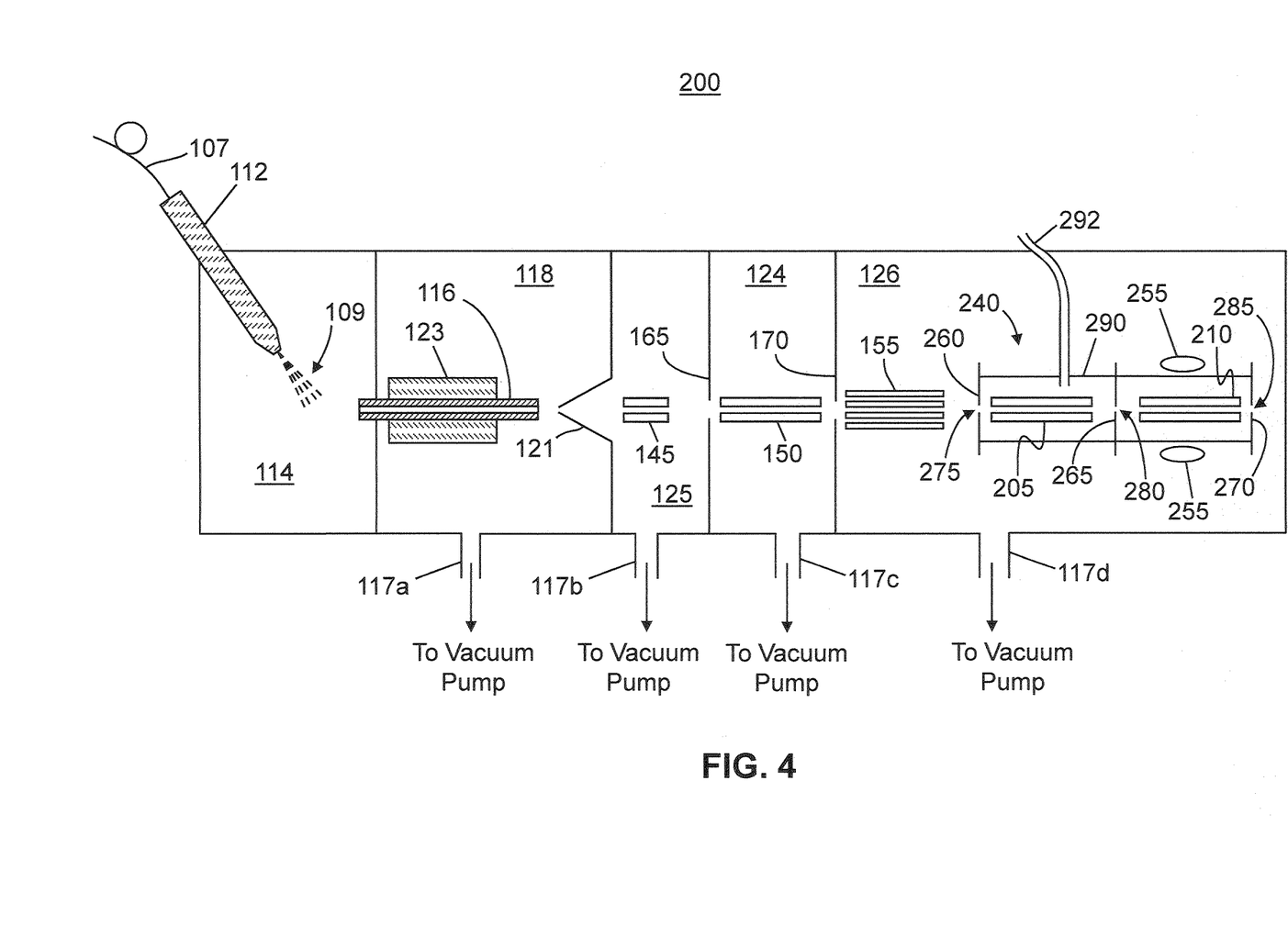
FIG. 4 is a symbolic diagram of a mass spectrometer that includes a differential-pressure dual ion trap mass analyzer.
Figure 5:
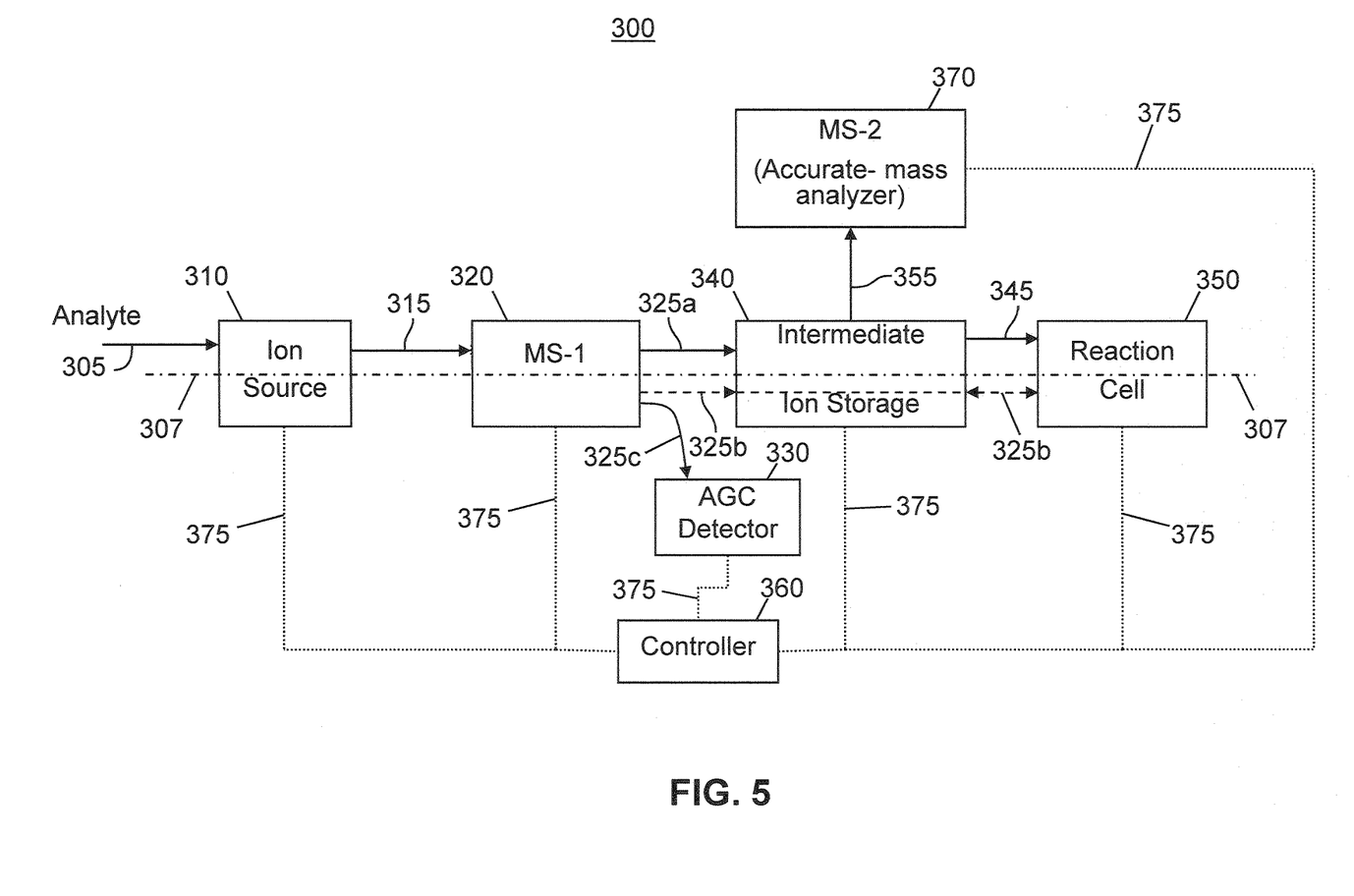
FIG. 5 is a schematic illustration of a second example of a generalized mass spectrometer system on which the invention according to some of its aspects may be practiced.

In Step 18 of the method 10 (FIG. 1), the selected precursor ion is fragmented, possibly in a collision cell as shown in and discussed with regard to FIG. 3, so as to yield a first-generation of product ions. The fragmentation, at this step, is such that the mass tags or labels on the selected precursor ion remain bonded to the analyte portion of the selected precursor ion—that is, the fragmentation is such that the tags or labels are not released from the selected precursor ion at this stage. This step may be accomplished, for example, by performing collision-induced fragmentation at low collision energy in a collision cell component such that only molecular backbone bonds are broken. In the optional step 20, these fragment ions are mass analyzed, thus generating $MS^2$ spectrum data. The mass analysis may occur in an ion trap component of the mass spectrometer system, such as the ion trap components illustrated in (and discussed following with reference to) FIGS. 2-3. Alternatively, the mass analysis may be performed in an accurate-mass mass analyzer component of the mass spectrometer system, as is illustrated in FIGS. 4-5 and discussed in greater detail with reference thereto. In the optional step 22, the analytes are identified on the basis of the $MS^1$ and $MS^2$ data. For instance, if the accurate-mass mass analyzer is capable of ppm mass accuracy, then a precursor mass and $MS^2$ spectrum is often sufficient to unambiguously identify the compound when coupled with a fragment predictor algorithm and a database search. The Step 22 may be eliminated if there is a high confidence that the spectrum data will adopt a certain known form or distribution of ions, as in the case where known materials are being introduced into the mass spectrometer system.

In Step 24 of the method 10 (FIG. 1), a plurality of first-generation product ions are co-isolated so as to be subsequently fragmented, in Step 26. In conventional systems, only a single ion is isolated for second-stage fragmentation. However, according to the present teachings, multi-notch isolation (discussed following with reference to FIG. 2) may be employed so as to co-isolate more than one fragment ion. Alternatively, a plurality of individual first-generation product ions of different mass-to-charge ratios could be isolated and transferred, one ion at a time, to an ion storage component (for example, the intermediate ion storage component 340 illustrated in FIG. 5) where the various first-generation product ions are accumulated. The isolation (Step 24) may be carried out using an ion trap component of the mass spectrometer system, such as mass analyzer component 136 of FIG. 3 (if implemented as a quadrupole ion trap) or high-pressure ion trap component 205 of FIG. 4. The fragmentation (Step 26) is carried out in a fashion, for example by a method employing a higher dissociation energy than the collision energy employed in the first fragmentation step, so as to specifically release the tagging or labeling components, thereby generating diagnostic fragments (second-generation product ions) comprising known masses. In the subsequent Step 28, the second-generation fragments are mass analyzed so as to generate $MS^3$ spectrum data.

Finally, in Step 30 of the method 10 (FIG. 1) analyte amounts are quantified or analyte ratios are determined using the detected intensities of the tag or label fragments determined from the $MS^3$ data of released tags. For example, a labeled analyte could be analyzed concurrently with a labeled standard in the same sample, wherein the labels are such that the analyte and standard have the same mass and chemical structure. Under such experimental conditions, the ratio of detected intensities of the different released labels could allow quantification of the analyte, since the concentration of the standard in the sample will generally be known. As another example, a sample of a labeled peptide from a first source could be analyzed together with a second sample the same peptide, differently labeled, from a second source, wherein the labels are such that the peptides and their first-generation fragments are indistinguishable from one another. In this case, the ratios of the intensities of the labels, as identified in the $MS^3$ spectra, may provide information relating to the relative concentrations of the peptide in the two sources. The first and second sample sources may be associated with different treatments or physical or biological conditions applied to the peptide in the sources.

The use of multi-notch isolation, as described in method 10, can increase the sensitivity of the $MS^3$ experiment up to N-fold, where N is the number of $MS^2$ fragments selected and co-isolated. One minor drawback is that, for each additional fragment that is maintained in the trap, the level of interference is also expected to increase N-fold. Since the percentage of interference in the basic $MS^3$ experiment is estimated to be approximately 1%, N values of 4 to 5 can provide significant sensitivity increases without dramatic impact on ratio accuracy.

FIG. 2 is a schematic diagram of a hypothetical mass spectrum plotted together with an overlaid plot of percentage of ions ejected as a function of mass-to-charge ratio when multi-notch ion isolation is applied. The hypothetical mass spectrum is shown as vertical solid lines along the mass-to-charge (m/z) shown as increasing from left to right and corresponding to an intensity scale at the left of the plot. The dashed line 90 indicates the percentage of ions ejected as a function of mass-to-charge ratio and corresponds to the percentage-of-ions-ejected (% Ejection) scale at the right of the plot. Under the application of multi-notch isolation to an ion trap, ions of all mass-to-charge ratios are ejected from the trap with the exception of certain mass-to-charge windows (notches) of interest. Ions whose m/z values are within any of the windows of interest will not be ejected from the ion trap and thus such ions will be co-isolated within the ion trap. The hypothetical plot of FIG. 2 illustrates three such notches, denoted as notch 92, notch 94 and notch 96. The notches are chosen so as to isolate particular ions of interest within the trap, upon ejection of ions whose m/z ratios are not within any of the notches. In the hypothetical plot of FIG. 2, the notches 92, 94 and 96 respectively correspond to ion peaks 93, 95 and 97.

As is known, an ion's motion within an ion trap can be excited by resonating the ion at one or more of their characteristic frequencies using a supplementary AC field (in addition to the trapping RF quadrupole and, possibly, DC fields). The supplementary AC field is superposed on the main quadrupole field by applying a relatively small oscillating (AC) potential to the appropriate electrodes. To excite the motion of ions having a particular m/z, the supplementary AC field includes a component that oscillates at or near the characteristic frequency of the ions' motion. If ions having more than one m/z are to be excited, the supplementary field can contain multiple frequency components that oscillate with respective characteristic frequencies of each m/z to be resonated.

To generate the supplementary AC field, a supplementary waveform is generated by a waveform generator, and the voltage associated with the generated waveform is applied to the appropriate electrodes by a transformer. The supplementary waveform can contain any number of frequency components that are added together with some relative phase. This waveform may be referred to as a resonance ejection frequency waveform or simply an ejection frequency waveform. These ejection frequency waveforms can be used to resonantly eject a range of unwanted ions from the ion trap.

When an ion is driven by a supplementary field that includes a component whose oscillation frequency is close to the ion's characteristic frequency, the ion gains kinetic energy from the field. If sufficient kinetic energy is coupled to the ion, its oscillation amplitude can exceed the confines of the ion trap. The ion will subsequently impinge on the wall of the trap or will be ejected from the ion trap if an appropriate aperture exists.

Because different m/z ions have different characteristic frequencies, the oscillation amplitude of the different m/z ions can be selectively increased by exciting the ion trap. This selective manipulation of the oscillation amplitude can be used to remove unwanted ions at any time from the trap. For example, an ejection frequency waveform can be utilized to isolate a narrow range of m/z ratios during ion accumulation when the trap is first filled with ions. In this way the trap may be filled with only the ions of interest, thus allowing a specific m/z range or ranges to be isolated within the ion trap.

Ion isolation can be performed using broadband resonance ejection frequency waveforms that are typically created by summing discrete frequency components represented by sine waves (as described in U.S. Pat. No. 5,324,939). That is, the summed sine waves have discrete frequencies corresponding to the m/z ranges of ions that one desires to eject but excluding frequency components corresponding to the m/z range of ions that one desires to retain. The omitted frequencies define one or more frequency notches in the ejection frequency waveform. The frequency components may be calculated by first choosing a desired multi-notch waveform and then calculating an inverse Fourier Transform of the desired waveform. Thus when the ejection frequency waveform is applied, ions having undesired m/z's can be essentially simultaneously ejected or otherwise eliminated while the desired m/z ions (within the one or more notches) are retained, because their m/z ratio values correspond to where the frequency components are missing from the ejection waveform. To eject or otherwise eliminate all undesired ions substantially simultaneously, the ejection frequency waveform needs to include closely spaced discrete frequency components. Thus the ejection frequency waveform is typically generated from a large number of sine waves.

In accordance with methods according to the present teachings, the mass spectrum of FIG. 2 will generally be a mass spectrum of fragment ions produced by fragmentation (such as by collision induced dissociation) of precursor ions derived from a sample containing isobarically-labeled compounds. In other words, the mass spectrum of FIG. 2 will generally be an $MS^2$ spectrum or a spectrum produced from an $MS^2$ analysis. The analytes, in such cases, will generally comprise ions derived from proteins or peptides and comprising a plurality of respective mass-to-charge (m/z) ratios. In accordance with methods according to the present teachings, ions corresponding to peaks 93, 95 and 97 will generally correspond to particular fragment ions that are known to be or believed to be fragments of precursor ions derived from isobarically-labeled compounds (analytes or standards or both) of interest. Each protein or peptide analyte may produce a plurality of such fragment ions—each comprising a different respective m/z ratio. Thus, in accordance with methods according to the present teachings, the co-isolated fragments corresponding to peaks 93, 95 and 97 will generally be simultaneously transferred to a collision cell for fragmentation so as to generate an $MS^3$ spectrum.

Figure 6:
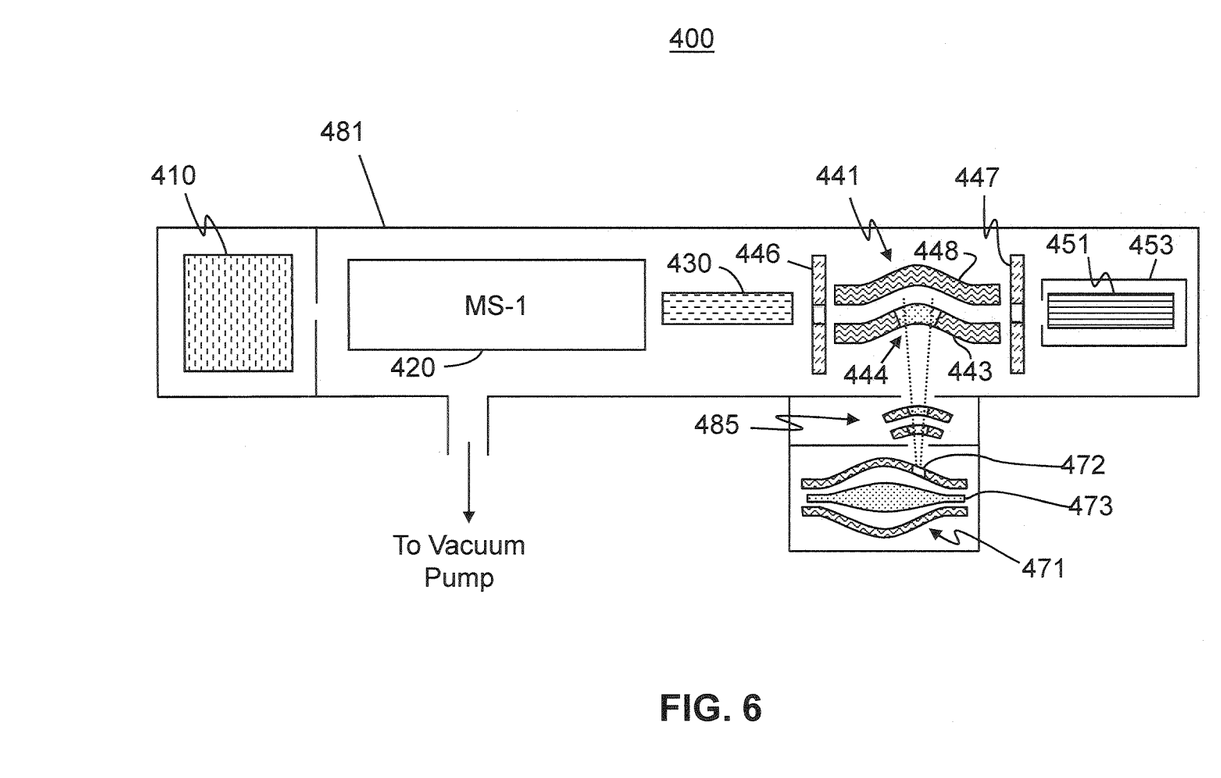
FIG. 6 is a schematic illustration of an electrostatic-trap-type mass spectrometer in which both collisional ion dissociation and electron transfer dissociation may be performed and on which the present invention, in accordance with some of its aspects, may be practiced.

FIGS. 5-6, described later in this document provide general and specific examples of mass spectrometer systems on which the invention may be practiced according to various of its aspects. Prior to discussing FIGS. 5-6, however, examples of conventional mass spectrometer systems are provided in FIGS. 3-4 in order to illustrate general operating principles and instrument features which may be employed, in part, in the practice of the invention.

FIG. 3 is a schematic illustration of an example of a conventional ion trap mass spectrometer system, shown generally at 100, capable of providing collisional ion dissociation. Referring to FIG. 3, an ion source 112 housed in an ionization chamber 114 is connected to receive an analyte-bearing liquid or gaseous sample from an associated apparatus such as for instance a liquid chromatograph or syringe pump through a capillary 107. As but one example, an atmospheric pressure electrospray source is illustrated. However, any ion source may be employed, such as a heated electrospray ionization (H-ESI) source, an atmospheric pressure chemical ionization (APCI) source, an atmospheric pressure matrix assisted laser desorption (MALDI) source, a photoionization source, or a source employing any other ionization technique. The ion source 112 forms charged particles 109 (either ions or charged droplets that may be desolvated so as to release ions) representative of the sample, which charged particles are subsequently transported from the ion source 112 to the mass analyzer 136 in high-vacuum chamber 126 through intermediate-vacuum chambers 118 and 125 of successively lower pressure in the direction of ion travel. In particular, the droplets or ions are entrained in a background gas and transported from the ion source 112 through an ion transfer tube 116 that passes through a first partition element or wall 115a into an intermediate-vacuum chamber 118 which is maintained at a lower pressure than the pressure of the ionization chamber 114 but at a higher pressure than the pressure of the high-vacuum chamber 126. The ion transfer tube 116 may be physically coupled to a heating element or block 123 that provides heat to the gas and entrained particles in the ion transfer tube so as to aid in desolvation of charged droplets so as to thereby release free ions.

Due to the differences in pressure between the ionization chamber 114 and the intermediate-vacuum chamber 118 (FIG. 3), gases and entrained ions are caused to flow through ion transfer tube 116 into the intermediate-vacuum chamber 118. A second plate or partition element or wall 115b separates the intermediate-vacuum chamber 118 from a second intermediate-pressure region 125, likewise a third plate or partition element or wall 115c separates the second intermediate pressure region 125 from the high-vacuum chamber 126. A first ion optical assembly 120a provides an electric field that guides and focuses the ion stream leaving ion transfer tube 116 through an aperture 122 in the second partition element or wall 115b that may be an aperture of a skimmer 121. A second ion optical assembly 120b may be provided so as to transfer or guide ions to an aperture 127 in the third plate or partition element or wall 115c and, similarly, another ion optical assembly 120c may be provided in the high vacuum chamber 126 containing the mass analyzer 136. The ion optical assemblies or lenses 120a-120c may comprise transfer elements, such as, for instance a multipole ion guide, so as to direct the ions through aperture 122 and into the mass analyzer 136. The mass analyzer 136 comprises one or more detectors 140 whose output can be displayed as a mass spectrum. Vacuum ports 113a, 113b and 113c may be used for evacuation of the various vacuum chambers.

It is to be understood that the mass spectrometer system 100 (as well as other such systems illustrated herein) is in electronic communication with a controller (not illustrated), which includes hardware and/or software logic for performing data analysis and control functions. Such controller may be implemented in any suitable form, such as one or a combination of specialized or general purpose processors, field-programmable gate arrays, and application-specific circuitry. In operation, the controller effects desired functions of the mass spectrometer system (e.g., analytical scans, isolation, and dissociation) by adjusting voltages (RF, DC and AC voltages provided by various not-illustrated power supplies) applied to the various electrodes of ion optical assemblies 120a-120c and quadrupoles or mass analyzers 132, 134 and 136, and also receives and processes signals from detectors 140. The controller may be additionally configured to store and run data-dependent methods in which output actions are selected and executed in real time based on the application of input criteria to the acquired mass spectral data. The data-dependent methods, as well as the other control and data analysis functions, will typically be encoded in software or firmware instructions executed by the controller.

As illustrated in FIG. 3, the conventional ion trap mass spectrometer system 100 is a triple-quadrupole system comprising a first quadrupole device 132, a second quadrupole device 134 and a third quadrupole device 136, the last of which is a mass analyzer comprising ion detectors 140. The mass analyzer 136 may be implemented as a quadrupole ion trap. Various modes of operation are known. In many modes of operation, the first quadrupole device is operated as an ion trap which is capable of retaining and isolating selected precursor ions (that is, ions of a certain mass-to-charge ratio or ratios, m/z) which are then transported to the second quadrupole device 134. In other modes of operation, the first quadropole device is operated as an ion filter which transmits only ions of certain mass-to-charge ratio or ratios to the second quadrupole device. In many modes of operation, the second quadrupole device 134 is employed as a fragmentation device which causes collision induced fragmentation of the selected precursor ions through interaction with molecules of an inert collision gas introduced through tube 135. The second quadrupole 134 may be operated as an RF/DC device which functions as an ion filter. The precursor or fragment ions are transmitted from the second quadrupole device 134 to the third quadrupole device 136 for mass analysis of the various ions.

As discussed above, mass spectrometer system 100 (FIG. 3) includes a triple-quadrupole component. The triple-quadrupole component may be incorporated into a single mass spectrometer system that also includes an accurate-mass mass analyzer, such as a time-of-flight (TOF) mass analyzer, a Fourier-Transform Ion Cyclotron resonance (FT-ICR) mass spectrometer or an electrostatic trap mass analyzer, an example of which is the Orbitrap™ mass analyzer. The accurate-mass mass analyzer preferably is capable of at least 5 ppm accuracy and, even more preferably, is capable of at least 1 ppm accuracy. In such instances, either precursor or product ions that are analyzed or produced in the triple-quadrupole component may be passed to the accurate-mass mass analyzer system. The accurate-mass mass analyzer system may then be employed to perform further or alternative analyses on the passed-through ions. The single mass spectrometer system may also include a different type of fragmentation or reaction cell within which the passed-through ions may be further fragmented or manipulated. FIG. 5, discussed below, provides a generalized system illustrating these principles.

FIG. 4 depicts the components of a mass spectrometer 200 in which a differential-pressure dual cell ion trap mass analyzer may be implemented. The mass spectrometer 200 is described in greater detail in United States Patent Application Publication 2010/0148063 assigned to the assignee of the present invention and incorporated herein by reference in its entirety. The ion source, 112, ionization chamber 114, ion transfer tube 116, heating element or block 123 and skimmer 121 are as described previously in regard to FIG. 3. The ions are transported from ionization chamber 114, which for an electrospray source will typically be held at or near atmospheric pressure, through several intermediate chambers 118, 125 and 124 of successively tower pressure, to a vacuum chamber 126 in which differential-pressure dual ion trap mass analyzer 240 resides. Efficient transport of ions from ion source 112 to mass analyzer 240 is facilitated by a number of ion optic components, including quadrupole RF ion guides 145 and 150, octopole RF ion guide 155, skimmer 121, and electrostatic lenses 165 and 170. Ions may be transported between ionization chamber 114 and the first intermediate chamber 118 through the ion transfer tube 116. Intermediate chambers 118, 125 and 124 and vacuum chamber 126 are evacuated by a suitable arrangement of pumps connected to vacuum ports 117a-117d to maintain the pressures therein at the desired values.

Dual ion trap mass analyzer 240 includes first and second quadrupole traps 205 and 210 positioned adjacent to one another. For reasons that will become evident in view of the discussion set forth below, first quadrupole ion trap 205 will be referred to as the high-pressure trap (HPT), and second quadrupole ion trap 210 will be referred to as the low-pressure trap (LPT). It is noted that the term "adjacent", as used herein to describe the relative positioning of HPT 205 and LPT 210, is intended to denote that HPT 205 and LPT 210 are positioned in close proximity, but does not exclude the placement of one or more ion optic elements between the two traps—in fact, the preferred embodiment requires such an ion optic element.

Generally described, a two-dimensional quadrupole ion trap may be constructed from four rod electrodes disposed about the trap interior. The rod electrodes are arranged into two pairs, each pair being opposed across the central longitudinal axis of the trap. In order to closely approximate a pure quadrupole field when the RF voltages are applied, each rod is formed with a truncated hyperbolic surface facing the trap interior. In other implementations, round (circular) or even planar (flat) electrodes can be substituted for the hyperbolic electrodes. In some implementations, each rod electrode is divided into three electrically isolated sections, consisting of front and back end sections flanking a central section. Sectioning of the rod electrodes allows the application of different DC potentials to each of the sections, such that ions may be primarily contained within a volume extending over a portion of the length of the trap. For example, positive ions may be concentrated within a central volume of the trap interior (which is roughly longitudinally co-extensive with the central sections of the rod electrodes) by raising the DC potential applied to the end sections relative to the central sections.

A generally tubular enclosure 290 engages and seals to front lens 260, inter-trap lens 265 and back lens 270 to form an enclosure for HPT 205 and LPT 210. This arrangement enables the development of the desired pressures within HPT 205 and LPT 210 by restricting communication between the two traps and between each trap and the exterior region to flows occurring through the various apertures. Enclosure 290 may be adapted with elongated apertures to permit passage of ejected ions to detectors 255. A buffer gas, typically helium, is added to the interior of HPT 205 via a conduit 292 that penetrates sidewall 290. The pressures that are maintained within HPT 205 and LPT 210 will depend on the buffer gas flow rate, the sizes of lens apertures 275, 280 and 285, the pressure of vacuum chamber 126, the construction of enclosure 290 (including any apertures formed therein) and the associated pumping speed of the pumping port for vacuum chamber 126. Oscillating voltages, including the main RF (trapping) voltage and supplemental AC voltages (for resonant ejection, isolation and CID), are applied to the electrodes of HPT 205 and LPT 210 by an RF/AC controller (not illustrated). DC voltages are respectively applied to the electrodes of HPT 205 and LPT 210 by respective DC controllers (not illustrated).

Broadly described, therefore, the mass spectrometer 200 includes a dual-trap mass analyzer. The dual-trap mass analyzer includes adjacently disposed first and second two-dimensional quadrupole ion traps operating at different pressures. The first ion trap has an interior volume maintained at a relatively high pressure, for example in the range of $5.0 \times 10^{-4}$ to $1.0 \times 10^{-2}$ Torr of helium, to promote efficient ion trapping, kinetic/spatial cooling, and fragmentation via a CID process. The cooled (and optionally fragmented) ions are transferred through at least one ion optic element to the interior of the second ion trap, which is maintained at a significantly lower buffer gas pressure (for example, in the range of $1.0 \times 10^{-5}$ to $2.0 \times 10^{-4}$ Torr of helium) relative to the first ion trap pressure. The lower pressure in the second ion trap facilitates the acquisition of high-resolution mass spectra and/or use of higher scan rates while maintaining comparable m/z resolutions, and may also enable the utilization of reduced-q resonant ejection without incurring unacceptable levels of chemically dependant mass shift. In addition, the lower pressure region also allows the possibility of higher resolution ion isolation.

The dual-trap mass analyzer of the mass spectrometer system 200 may be operated in a number of different modes. In one mode, ions are trapped and cooled in the first ion trap, and then transferred to the second ion trap for mass analysis (the term "mass analysis" is used herein to denote measurement of the mass-to-charge ratios of the trapped ions). In another mode, ions are trapped and cooled in the first trap, and precursor ions are selected (isolated) for fragmentation by ejecting from the first trap all ions outside of a mass-to-charge range of interest. In accordance with the CID technique, the precursor ions are then kinetically excited and undergo energetic collisions with the buffer gas to produce product ions. The product ions are then transferred to the second ion trap for mass analysis. Yet another mode of operation makes use of the potential for high-resolution isolation in the second ion trap. In this mode, ions are trapped and cooled in the first ion trap and then transferred into the second ion trap. Precursor ions are then isolated in the second ion trap by ejecting all ions outside of a mass-to-charge range of interest. Due to the low pressure within the second ion trap, isolation may be effected at higher resolution and greater efficiency (less loss of precursor ions) than is attainable at higher pressures, so that precursor ion species may be selected with greater specificity. The precursor ions are then transferred back into the first ion trap and are thereafter fragmented by the aforementioned CID technique. The resulting product ions are then transferred into the second ion trap for mass analysis. In a variant of this mode of operation, the precursor ions are accelerated to high velocities during transfer from the second ion trap to the first ion trap (by application of appropriate DC voltages to the rod electrodes and/or inter-trap lens) to produce a fragmentation pattern that approximates that occurring in the collision cell of conventional triple-stage quadrupole mass filter instruments. Other known dissociation or reaction techniques, including without limitation photodissociation, electron transfer dissociation (ETD), electron capture dissociation (ECD), and proton transfer reactions (PTR) may be used in place of or in addition to the CID technique to yield product ions. The product ions may then be transferred back into the second ion trap for mass analysis.

The dual-trap mass analyzer of the mass spectrometer system 200 (FIG. 4) may be incorporated into a single mass spectrometer system that also includes an accurate-mass mass analyzer, such as a time-of-flight (TOF) mass analyzer, a Fourier-Transform Ion Cyclotron resonance (FT-ICR) mass spectrometer or an electrostatic trap mass analyzer, an example of which is the Orbitrap® mass analyzer. The accurate-mass mass analyzer is preferably is capable of at least 5 ppm accuracy and, even more preferably, is capable of at least 1 ppm accuracy. In such instances, either precursor or product ions that are analyzed or produced in the dual-trap mass analyzer may be passed to the accurate-mass mass analyzer system. The accurate-mass mass analyzer system may then be employed to perform further or alternative analyses on the passed-through ions. The single mass spectrometer system may also include a different type of fragmentation or reaction cell within which the passed-through ions may be further fragmented or manipulated. FIG. 5, discussed below, provides a generalized system illustrating these principles.

An example of a generalized mass spectrometer system 300 on which the invention according to some of its aspects may be practiced is shown in FIG. 5. Analyte material 305 is provided to an ion source 310 so as to generate ions 315. The ions are admitted to a first mass analyzer (MS$^1$) 320 that has mass analysis and mass selection functionality and in which, optionally, fragmentation may be performed. For instance, the first mass analyzer MS$^1$ may comprise an ion trap or quadrupole mass analyzers. Ion source 310 could be a MALDI source, an electrospray source or any other type of ion source. In addition, multiple ion sources may be used. Also, the mass analyzer MS$^1$ 120 may include any number of other stages of mass analysis, and/or fragmentation or other ion manipulation. It is to be noted that, in the system 300, ions are transferred from one component to the next via ion optics (e.g. RF multipoles) which, in some cases, are not specifically illustrated. Moreover, the drawings do not show the electrodes of the various parts that are used to guide, filter, fragment and/or trap ions within those parts.

An automatic gain control (AGC) detector 330 may be provided in the mass spectrometer system 300 to quantitatively measure or sample an ion flux or number of ions for purposes of controlling the number of ions in a subsequent ion population. Any of the known AGC methods may be used to determine the optimum ionization time for fills of the downstream intermediate ion storage 340 or the accurate-mass mass analyzer (MS$^2$) 370. Accordingly, a proportion of ions exiting MS$^1$ may be diverted along path 325c to AGC detector 330. Otherwise, ions are transferred from MS$^1$ along path 325a to the intermediate ion storage 340.

Still with reference to the system 300 shown in FIG. 5, selected ions are transferred from the first mass analyzer 320 along path 325a into the intermediate ion store 340 where they may be captured and trapped. The intermediate ion store 340 may comprise, for instance, an ion trap device. Ions released from the intermediate ion store 340 may be transferred along path 355 to an accurate-mass mass analyzer (MS²) 370. The accurate-MS may receive, for analysis, either unfragmented precursor ions, a set of ions formed by fragmentation of a single selected precursor ion, or a mixture of a plurality of sets of ions, each such set formed by fragmentation of a different respective precursor ion. With reference to the systems illustrated herein, ions produced using the optimum ionization time may be fragmented in either the first mass analyzer 320 or a separate reaction cell 350, for example, by collision-induced dissociation. The accurate-mass mass-analyzer (MS²) 370 has sufficiently high m/z resolution to resolve most or all species in such mixed ion populations. Examples of suitable accurate-mass mass analyzers are ion cyclotron resonance mass spectrometers and electrostatic trap mass spectrometers, such as the Orbitrap® mass analyzer.

A controller 360, which may comprise a general purpose computer or, perhaps, a specialized electronic logic device, is electronically coupled to other components along electronic control lines 375. The electronic control lines 375 may send control signals from the controller 360 to the mass spectrometers, intermediate ion storage device, ion source, the various ion optics, etc. in order to control the coordinated operation of these components. For instance, the controller may send signals to set potentials on the electrodes of the various parts at the various appropriate times. The electronic control lines 375 may also transmit signals from one or more of the components of the system 300 back to the controller 360. For instance, the controller 360 may receive signals from the AGC detector 330 and from the accurate-mass MS 370, such signals relating to number of ions detected.

The system 300 shown in FIG. 5 provides for two types of ion pathways between the first mass analyzer MS¹ 320 and the accurate-mass mass analyzer MS² 370, corresponding to two respective modes of operation. In a first mode of operation, selected ions are delivered along pathway 325a from MS¹ to the intermediate ion storage device 340 where they are trapped. Once a suitable time delay has passed, the controller 360 may cause the ions to be transported to the reaction cell 350 for fragmentation or other manipulation so as to produce fragment or product ions. In a second, alternative, mode of operation, the intermediate ion storage device 340 is used merely as an ion guide ("transmission mode") such that ions are transferred along pathway 325b (which may, in fact be coincident with path 325a but which is shown offset from that pathway, for clarity) from MS¹ to the reaction cell 350. The intermediate ion store 340 may have a gas introduced therein, thereby reducing the energy of the ions through collisional cooling as they pass through the intermediate ion store and enter the reaction cell 350.

Precursor ions or pre-existing fragments may be fragmented in the reaction cell 350. Pre-existing fragments may be produced, for instance, in MS¹ 320. Ion fragmentation may be effected by any suitable fragmentation technique, such as collision-induced dissociation (CID). The resulting fragment ions (if any) or precursor ions (if any) are then transferred, in the opposite direction, back along path 325b from the reaction cell to the intermediate ion storage device 340. After storage in the intermediate ion storage device 340 for an appropriate time, these fragment ions are transferred to the accurate-mass MS 370 for analysis along pathway 355. Multiple fills of the accurate-mass MS 370 may be formed using different respective processing techniques (for instance, high energy versus low energy fragmentation) in the reaction cell 350. The flexibility provided by these various operation options provides the capability of performing both precursor ion as well as fragment ion analyses using the accurate-mass MS.

FIG. 6 illustrates another example of a mass spectrometer system 400 on which the invention according to some of its aspects may be practiced. The mass spectrometer system 400 shown in FIG. 6 is a specific implementation of the generalized system 300 illustrated in FIG. 5 and comprises, as an accurate-mass mass analyzer, an electrostatic trap mass analyzer such as an Orbitrap® mass analyzer 471. In the illustrated system, ions provided by ion source 410 are transferred to one or more evacuated chambers enclosed by housing 481. The ions are transferred or guided by ion optics (not shown) so as to be admitted to a first mass analyzer system 420. The mass analyzer system 420 may comprise one or more stages of any of mass filters, collision or reaction cells, ion traps or detectors. The mass analyzer system 420 may thus comprise may comprise mass analysis or mass selection functionality and may, optionally, provide the capability to perform collision induced fragmentation of precursor ions so as to produce a first generation of fragment ions. For example, the mass analyzer system 420 may comprise some or all of the components to the right of ("downstream" from) the ion source and ionization chamber of either FIG. 3 or FIG. 4. Accordingly, the mass analyzer system 420 may provide all the functionality of either the mass spectrometer system 100 (FIG. 3) or the mass spectrometer system 200 (FIG. 4) together with the added functionality provided by the accurate-mass mass analyzer and reaction cell 451.

Within the mass spectrometer system 400 (FIG. 6), selected isolated ions or ion fragments may be transferred, by means of ion optics 430, from the first mass analyzer system 420 to a curved quadrupole trap 441 (also known as a "C-trap") that has a slot 444 in an inner electrode 443. In operation, the curved curved quadrupole trap 441 serves as an intermediate ion store which may acquire ions from either end and from which such acquired or accumulated ions may be injected into the electrostatic trap (e.g., Orbitrap®) mass analyzer 471. Prior to ion injection, ions may be squeezed along the axis of the curved quadrupole trap 441 by raising voltages on end electrodes 446 and 447. For ion injection into the Orbitrap® mass analyzer 471, the RF voltage on the curved quadrupole trap 441 is switched off, as is well known. Pulses are applied to electrodes 443 and 448 and to an electrode of curved ion optics 485 so that the transverse electric field accelerates ions into the curved ion optics 485. The converging ion beam that results enters the mass analyzer 471 through injection slot 472. The ion beam is squeezed towards the axis by an increasing voltage on a central electrode 473. Due to temporal and spatial focusing at the injection slot 472, ions start coherent axial oscillations. These oscillations produce image currents that are amplified and processed. Further details of the electrostatic trap apparatus 471 are described in International Application Publication WO 02/078046, U.S. Pat. No. 5,886,346, U.S. Pat. No. 6,872,938.

The system 400 shown in FIG. 6 optionally further comprises a reaction cell 451, which may comprise a collision cell (such as an octopole) that is enclosed in a gas tight shroud 453 and that is aligned to the curved quadrupole trap 441, as shown in FIG. 6. The reaction cell 451, when used as a collision cell, may be supplied with an RF voltage of which the DC offset can be varied. A collision gas line (not shown) may be attached and the cell is pressurized with nitrogen (or other) gas. Higher energy collisions (HCD) may take place in the system 400 as follows: Ions of a determined number, either mass selected or not, are transferred from the first mass analyzer system 420 (MS 1) to the curved quadrupole trap 441. For HCD, ions are emitted from the curved quadrupole trap 441 to the octopole of the reaction cell 451 by setting a voltage on a trap lens. Ions collide with the gas in the reaction cell 451 at an experimentally variable energy which may be represented as a relative energy depending on the ion mass, charge, and also the nature of the collision gas (i.e., a normalized collision energy). Thereafter, the product ions are transferred from the reaction cell 451 back to the curved quadrupole trap 441 by raising the potential of the octopole. A short time delay (for instance 30 ms) is used to ensure that all of the ions are transferred. In the final step, ions are ejected from the curved quadrupole trap 441 into the Orbitrap® analyzer (or other accurate-mass mass analyzer) 471 as described previously. HCD can be used to generate a series of ions which are typical of higher-energy fragmentation processes. The net outcome of such a procedure is the observation of some diagnostic ions which are not normally seen during conventional CID fragmentation. In the system 400 shown in FIG. 6, collision induced fragmentation may be performed in a collision cell or high-pressure ion trap of the first mass analyzer system 420. Alternative or supplemental higher energy collision fragmentation (HCD) may be performed the reaction cell 451.

Multiple fill experiments may be performed in the system 400 as follows: Ions from the first mass analyzer system 420 are injected multiple times into the curved quadrupole trap 441. Ions from first mass analyzer system 420 can be of the same type or they can be different, viz., mass isolated, collision activated, higher order collision activated, etc. Multiple energy HCD experiments are performed by passing ions from the first mass analyzer system 420, following each individual fill in the ion trap, into the reaction cell 451, here used as an ion store, at different collision energy offsets. The sum of fragment ions from all fills in the reaction cell are transferred to the curved quadrupole trap 441 where they are then ejected into the Orbitrap analyzer (or other accurate-mass mass analyzer) 471. Likewise, a population of ions can be built up in the curved quadrupole trap 441 through multiple fills from the $MS^1$ 420 and then sent to the reaction cell 451, or, alternatively, sent directly to the Orbitrap® analyzer 471.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Accordingly, many modifications may be made by one of ordinary skill in the art without departing from the essence and scope of the invention. Neither the description nor the terminology is intended to limit the scope of the invention— the invention is defined only by the claims. Any technical publications, patent applications publications or patents mentioned herein are hereby incorporated by reference in their respective entirety.

What is claimed is:

1. A method for analyzing isobarically-labeled analyte compounds using a mass spectrometer, the method comprising the steps of:
    (a) ionizing a set of compounds including the isobarically-labeled analyte compounds provided from a sample so as to generate a plurality of precursor ion species comprising different respective mass-to-charge (m/z) ratios;
    (b) isolating a selected precursor ion species;
    (c) fragmenting the selected precursor ion species so as to generate a plurality of first-generation fragment ion species comprising different respective m/z ratios;
    (d) selecting and co-isolating a subset of the plurality of first-generation product ion species comprising two or more of the first-generation product ion species;
    (e) fragmenting the selected and isolated first-generation product ion species so as to generate a plurality of second-generation fragment ion species including released label ions;
    (f) generating a mass spectrum of the second-generation fragment ion species; and
    (g) generating quantitative information relating to at least one analyte compound based on peaks of the mass spectrum attributable to the released label ions.

2. A method as recited in claim 1, wherein the isobarically-labeled analyte compounds comprise isobarically-labeled proteins or peptides.

3. A method as recited in claim 1, wherein the step (c) of fragmenting the selected precursor ion species is performed using a collision energy that is insufficient to cause substantial fragmentation or release of the labels of the selected precursor ion species.

4. A method as recited in claim 1, wherein the isobarically-labeled analyte compounds comprise isobarically-labeled proteins or peptides and wherein the step (c) of fragmenting the selected precursor ion species is performed using a collision energy that is sufficient to cleave protein or peptide backbone bonds within the selected precursor ion species but that is insufficient to cause substantial fragmentation or release of the labels of the selected precursor ion species.

5. A method as recited in claim 1, wherein the set of compounds includes a labeled standard compound, wherein a first-generation fragment ion species generated from the labeled standard compound comprises a similar m/z ratio as a first-generation fragment ion species generated from one of the labeled analyte compounds, and wherein a concentration of said one of the labeled analyte compounds is determined, in step (e), by comparing a detected quantity of a label ion released from the standard compound with a detected intensity of a label ion released from said one of the labeled analyte compounds.

6. A method as recited in claim 1,
    wherein a first portion of an analyte compound is provided from a first source and a second portion of said analyte compound is provided from a second source;
    wherein the first and second portions of the analyte compound are provided with different respective labels such that a first-generation fragment ion species generated by ionization of the first portion of the analyte compound comprises a similar m/z ratio as a first-generation fragment ion species generated by ionization of the second portion of the analyte compound; and
    wherein a ratio between the concentrations of the analyte compound in the first and second sources is determined, in step (e), by comparing a detected quantity of the label ion released from the analyte compound from the first source with a detected intensity of the label ion released from the analyte compound from the second source.

7. A method as recited in claim 1, wherein the ion species of the subset of the plurality of first-generation product ion species are co-isolated by:
    introducing the plurality of first-generation product ion species into an ion trap; and
    resonantly ejecting, from the ion trap, ion species having m/z ratios other than the m/z ratios of the subset of the plurality of first-generation product ion species.

8. A method as recited in claim 1, wherein the step (b) of isolating a selected precursor ion species comprises co-isolating a plurality of selected precursor ion species, each selected precursor ion species corresponding to a respective different isobarically-labeled analyte compound.

9. An apparatus comprising:
   (a) an ion source configured to so as to generate a plurality of precursor-ion species having respective mass-to-charge (m/z) ratios from a plurality of isobarically-labeled analyte compounds comprising respective chemical labels;
   (b) at least one ion trap configured to receive the precursor ion species, to isolate a selected precursor ion species and to co-isolate a selected two or more of a plurality of first-generation product-ion species generated by fragmentation of the selected precursor ion species;
   (c) at least one fragmentation cell configured to fragment the isolated selected precursor ion species so as to generate the plurality of first-generation product-ion species and to fragment the selected two or more of the first-generation product-ion species so as to generate a plurality of second-generation product-ion species; and
   (d) a mass analyzer configured so as to separate and detect ion species of the plurality of precursor-ion species, of the plurality of first-generation product-ion species and of the plurality of second-generation product-ion species,
   wherein the at least one fragmentation cell is configured so as to fragment the isolated precursor ion species using a fragmentation energy or mechanism that is does not cause fragmentation or release of the labels and using a fragmentation energy or mechanism that fragments the selected two or more of the first-generation product-ion species such that label ions are released.

10. An apparatus as recited in claim 9, further comprising:
   (e) an electronic controller electronically coupled to the mass analyzer so as to receive data relating to detected intensities of the separated ion species therefrom, and comprising instructions operable to generate mass spectra from the received data and to generate quantitative information relating to at least one analyte compound based on mass spectral peaks attributable to the released label ions.

* * * * *